(12) United States Patent
Tissier et al.

(10) Patent No.: US 8,993,836 B2
(45) Date of Patent: Mar. 31, 2015

(54) PLANT PROMOTERS AND USES THEREOF

(75) Inventors: Alain Tissier, Pertuis (FR); Christophe Sallaud, Montpellier (FR); Denis Rontein, Greoux les Bains (FR)

(73) Assignee: Philip Morris Products S.A., Neuchatel (CH)

( * ) Notice: Subject to any disclaimer, the term of this patent is extended or adjusted under 35 U.S.C. 154(b) by 1138 days.

(21) Appl. No.: 11/664,153

(22) PCT Filed: Oct. 12, 2005

(86) PCT No.: PCT/FR2005/002530
§ 371 (c)(1),
(2), (4) Date: Mar. 29, 2007

(87) PCT Pub. No.: WO2006/040479
PCT Pub. Date: Apr. 20, 2006

(65) Prior Publication Data
US 2009/0300791 A1 Dec. 3, 2009

(30) Foreign Application Priority Data

Oct. 13, 2004 (FR) ..................... 04 10799

(51) Int. Cl.
| | | |
|---|---|---|
| C12N 15/82 | (2006.01) | |
| C12N 15/00 | (2006.01) | |
| C12N 5/10 | (2006.01) | |
| A01H 5/00 | (2006.01) | |
| C07H 21/04 | (2006.01) | |

(52) U.S. Cl.
CPC .................. *C12N 15/8223* (2013.01)
USPC ........ 800/278; 800/298; 800/317; 435/320.1; 435/419; 435/468; 536/24.1

(58) Field of Classification Search
None
See application file for complete search history.

(56) References Cited

U.S. PATENT DOCUMENTS

| 6,730,826 B2 | 5/2004 | Wagner et al. | |
|---|---|---|---|
| 2003/0100050 A1 * | 5/2003 | Wagner et al. | 435/69.1 |
| 2006/0260002 A1 * | 11/2006 | Ronen et al. | 800/278 |

FOREIGN PATENT DOCUMENTS

WO  WO 2004/111183 A2  12/2004

OTHER PUBLICATIONS

Wang et al (2001, NCBI Accession No. AF401234).*
Benfey et al (1989, EMBO J, 8(8):2195-2202).*
Ennajdaoui et al (2010, Plant Mol. Biol. 73:673-685).*
Benfey et al (1990, Science 250:959-966).*
Benfey et al (1989, EMBO J, 8(8):2195-2202.*
NCBI BLAST search with SEQ ID No. 10 Jan. 28, 2014.*
Ennajdaoui et al, Plant Mol Biol 73:673-85 (2010).*
Potenza_In Vitro Cell Dev Biol Plant_40_1_2004.*
Wagner, G. J. "Secreting Glandular Trichomes: More than Just Hairs", *Plant Physiol.*, 1991, pp. 675-679, vol. 96.
Wang, E. et al. "Isolation and characterization of the CYP71D16 trichome-specific promoter from *Nicotiana tabacum* L.", *Journal of Experimental Botany*, Sep. 2002, pp. 1891-1897, vol. 53, No. 376.
Wang, E. et al. "Elucidation of the functions of genes central to diterpene metabolism in tobacco trichomes using posttranscriptional gene silencing", *Planta*, 2003, pp. 686-691, vol. 216.
Ennajdaoui, H. et al. "Trichome specific expression of the tobacco (*Nicotiana sylvestris*) cembratrien-ol synthase genes is controlled by both activating and repressing *cis*-regions", *Plant Mol. Biol..*, 2010, pp. 673-685, vol. 73, XP-002592452.

* cited by examiner

*Primary Examiner* — Medina A Ibrahim
*Assistant Examiner* — Russell Boggs
(74) *Attorney, Agent, or Firm* — Saliwanchik, Lloyd & Eisenschenk (57) ABSTRACT

The invention concerns tools, methods and compositions for modifying plants and/or protein expression in plants. The invention concerns in particular transcriptional promoters enabling specific expression in the trichomes, constructs containing said promoters, and their uses for genetically modifying cells, seeds or plants. The invention also concerns methods for producing transgenic plants expressing proteins or metabolites of interest. The invention is generally applicable to any plant having glandular trichomes, and to the expression of any protein of industrial interest, in particular therapeutic or phytosanitary.

22 Claims, 4 Drawing Sheets

```
NsTPS02a-Prom1kb    1  AATTTATTTTCATAAAACTTCTCTAATTTTTGAACAAAATCTTATATTGATTTTTT.AAT
NsTPS02b-Prom1kb    1  AATTTATTTTTGTAAAACTTCTCTAATTTTTGGACAAACTCTTATATTGATTTTTT.AAT
NsTPS04-Prom1Kb     1  AATTTATTTTCGTAAAATTTCTCTAATTTTTGGACAAACTCTTATATTGGTTTTTT.AAT
NsTPS03-Prom1kb     1  AATTTATTTTCGTAAAATTTCTCTAATTT..GGACAAACTCTTATATTGATTTTTTTAAT
Consensus           1  AATTTATTTTCGTAAAACTTCTCTAATTTTTGGACAAACTCTTATATTGATTTTTT.AAT NsTPS02a-Prom1kb   60  CAAAGCCAAAATATTTATTTAACTATGAAAATTTTTT.AACAACTAATTTATTATGGTAA
NsTPS02b-Prom1kb   60  CAAAGCCAAAATATTTATTTAACTATGAAAAAATTTT.AACAACTAATTTATTATGGTAA
NsTPS04-Prom1Kb    60  CAAAGCCAAAATATTTATTTAACTATGAAATTTTGTTGAACAACTAATTTATTATGGTAA
NsTPS03-Prom1kb    59  CAAAGCCAAAATATTTATTTAACTATGAAAATTTTTT.AACAACTAATTTATTATGGTAA
Consensus          60  CAAAGCCAAAATATTTATTTAACTATGAAAATTTTTT.AACAACTAATTTATTATGGTAA NsTPS02a-Prom1kb  119  ATAATATTGATATGGTAACTTCAAGCACATGACAAAAATTATAACTAACTGCAGAAGTTT
NsTPS02b-Prom1kb  119  ATAATATTGATATGGTAACTTCAAGCACATGACAAAAATTATAACTAACTGCAGAAGTTT
NsTPS04-Prom1Kb   120  ATAATATTGATATGGTAACTTCAAGCACATGACAAAAATTATAACTAACTGCAGAAGTTT
NsTPS03-Prom1kb   118  ATAATATTGATATGGTAACTTCAAGCACATGATAAAAATTATAACTAACTGCAGAAGTTT
Consensus         119  ATAATATTGATATGGTAACTTCAAGCACATGACAAAAATTATAACTAACTGCAGAAGTTT NsTPS02a-Prom1kb  179  ACTGTCTCTCTGAATCTTGTGGCTATGTCATTCTATCATAACAAATACTTGTAGCTAATA
NsTPS02b-Prom1kb  179  ATTGTCTCTCTGAATCTTGTGGCTAT........ATCATAACAAATACTTGTAGCTAATA
NsTPS04-Prom1Kb   180  ACTGTCTCTCTGAATCTTGTGGCTATATCATTCTAT.ATAACAAATACTTGTAGCTAATA
NsTPS03-Prom1kb   178  ACTGTCTCTTTGAATCTTGTGGTTATATCATTCTATCATAACAAATACTTGTAGCTAATA
Consensus         179  ACTGTCTCTCTGAATCTTGTGGCTATATCATTCTATCATAACAAATACTTGTAGCTAATA
                                                                      Motif_3

NsTPS02a-Prom1kb  239  CGCCAACGATGTTCTCGATTTCATATAATTTGAATTTTAAAATAGCTTTTAAATTTAATA
NsTPS02b-Prom1kb  231  AGCCAACGATGTTCTCGGTTTCATATAATTTGAATTTTAAAATAGTTTTTAAATTTAATA
NsTPS04-Prom1Kb   239  AGCCAACGATGTTCTCGGTTTCATATAATTTGAATTTTAAAATAGTTTTTAAATTTAATA
NsTPS03-Prom1kb   238  AGCCAACGATGTTCTCGGTTTCATATAATTTGAATTTTAAAATAGTTTTTAAATTTAATA
Consensus         239  AGCCAACGATGTTCTCGGTTTCATATAATTTGAATTTTAAAATAGTTTTTAAATTTAATA NsTPS02a-Prom1kb  299  TTTATTTCAAATCATTATTGTGACTAACATGTTATAACCGCAGTAATATTTGGAGATGCA
NsTPS02b-Prom1kb  291  TTTATTTCAAATCATTATTGTGGCTAACATGTTATAATCGCAGTAATATTTGGAGATGCA
NsTPS04-Prom1Kb   299  TTTATTTCAAATCATTATTGTGGCTAGCATGTTATAACCGCAGTAATATTTGGAGATGCA
NsTPS03-Prom1kb   298  TTTATTTCAAATTATTATTGTGGCTAACATGTTATAACCGCAGTAATATTTGGAGATGCA
Consensus         299  TTTATTTCAAATCATTATTGTGGCTAACATGTTATAACCGCAGTAATATTTGGAGATGCA
                                                          Motif_2

NsTPS02a-Prom1kb  359  ATACTTATATTTAGCTACAAAATTTTATTGTATCATAATAAGTTTGTAGCTATTAAGTTA
NsTPS02b-Prom1kb  351  ATACTTATATTTAGCTACAAAATTTTATTGTATCAGAATAAGTTTGTAGCTATTAAGTTA
NsTPS04-Prom1Kb   359  ATACTTATATTTAGCTACAAAATTTTATTGTATCAGAATAAGTTTGTAACTATTAAGTTA
NsTPS03-Prom1kb   358  ATACTTATATTTAGCTTGAAAATTTTATTGTATCAGAACAAGTTTGTAGCTATTAAGTTA
Consensus         359  ATACTTATATTTAGCTACAAAATTTTATTGTATCAGAATAAGTTTGTAGCTATTAAGTTA
                              Motif_3                        Motif_3
```

FIGURE 1

```
NsTPS02a-Prom1kb   419 GTTTTTGCCACAAATTTTATAATTGAAGCAAAAATACCTATTCAACTACAATATTTTGT
NsTPS02b-Prom1kb   411 GTTTTTGCCACAAATTTTATAATTGAAGCAAAAATACTTATTCAGCTACAGTATTTTGT
NsTPS04-Prom1Kb    419 GTTTTTGCCACAAATTTTATAATTGAAGCAAAAATACCTATTCAGCTACGATATTTTGT
NsTPS03-Prom1kb    418 GTTTTTGCCACAAATTTTATAATTGAAGCAAAAATACCTATTCAGCTACAGTATTTTGT
Consensus          419 GTTTTTGCCACAAATTTTATAATTGAAGCAAAAATACCTATTCAGCTACAATATTTTGT NsTPS02a-Prom1kb   479 ATCGAGTAATATTTTGTGACTAGAAGATTAATATTATTACAGTAATTTCAGACGTGTGGC
NsTPS02b-Prom1kb   471 ATCGAGTAATATTTTGTGACTAGAAGATTAATATTGCTACAGTAATTTCAGACGTGTGGC
NsTPS04-Prom1Kb    479 ATCGAGTAATATTTTGTGACTAGAAGATTAATATTGCTAGAGTAATTTCAGACGTGTGGC
NsTPS03-Prom1kb    478 ATCGAGTAATATTTTGTGACTAGAAGATTAATATTGCTACAGTAATTTCAGACGTGTGGC
Consensus          479 ATCGAGTAATATTTTGTGACTAGAAGATTAATATTGCTACAGTAATTTCAGACGTGTGGC
                            Motif_2                          Motif_2

NsTPS02a-Prom1kb   539 AAAAACTCATAATTATCTACAAAATATTGTCGTAGCAATAATTTTTTATATCTATTAATC
NsTPS02b-Prom1kb   531 AAAAACTCATAATTAGCTACAAAATATTGTCGTAGCAATAATTTTTTATATCTATTAATG
NsTPS04-Prom1Kb    539 AAAAACTCATAATTAGCTACAAAATATTGTCGTAGCAATAATTGTTTATATCTATTAATC
NsTPS03-Prom1kb    538 AAAAACTCATAATTAGCTACAAAATATTGTCGTAGCAATAATTTTTTATATCTATTAATC
Consensus          539 AAAAACTCATAATTAGCTACAAAATATTGTCGTAGCAATAATTTTTTATATCTATTAATC
                                             Motif_1

NsTPS02a-Prom1kb   599 CAATTATTGCTACATGCTTTTATAACTTGAGGCAAAAATATCTATTTAGCTATAACATTT
NsTPS02b-Prom1kb   591 CAATTATTACTACATGCTTTTATAACTTGAGGCAAAAATATCTAAT.AGCTATAACATTT
NsTPS04-Prom1Kb    599 CAATTATTCCTATATGCTTTTATAACTTGAGCCAAAAATATTTATTTAGCTATAACATTT
NsTPS03-Prom1kb    598 CAATTATTGCTACATGCTTTTATAACTTGAGGCAAAAATATCTATTTAGCTATAACATTT
Consensus          599 CAATTATTGCTACATGCTTTTATAACTTGAGGCAAAAATATCTATTTAGCTATAACATTT
                               Motif_3

NsTPS02a-Prom1kb   659 TGTTAGAAGTAATTTTTGTGACTATAAAGTTGTTATTGCTACAGTAATTTCAAATGCGTG
NsTPS02b-Prom1kb   650 TGTTAGAAGTAATTTTTGTGGCTATAAAACTGGTATTGCTACAGTAATTTCAAATGCGTG
NsTPS04-Prom1Kb    659 TGTTAGAAGTAATTTTTGTGGCTATAAAGTTGTTATTGCTACGGTAATTTCAAATGCGTG
NsTPS03-Prom1kb    658 TATTAAAAGTAATTTTTGTGGCTATAAAGTTGTTATTGCTACAGTAATTTCAAATGCGTG
Consensus          659 TGTTAGAAGTAATTTTTGTGGCTATAAAGTTGTTATTGCTACAGTAATTTCAAATGCGTG
                              Motif_2                  Motif_3  Motif_2

NsTPS02a-Prom1kb   719 GCAAAAAAATACGATTAGCTACGAAATTTTATTGTAGCAATAAATTTGTAGCTATTTGG
NsTPS02b-Prom1kb   710 GCAAAAAAA.TACGATTAACTACGAAATTTTATTGTAGCAATAACTTTGTAGCTATTTGG
NsTPS04-Prom1Kb    719 GCAAACAAA.TACGATTAGCTACGAAATTTTATTGTAGCAATAAATTTGTAGCTATTTGG
NsTPS03-Prom1kb    718 GCAAAAAAATACGATTAGCTACGAAATTTTATTGTAGCAATAAATTTGTAGCTATTTGG
Consensus          719 GCAAAAAAA.TACGATTAGCTACGAAATTTTATTGTAGCAATAAATTTGTAGCTATTTGG
                                   Motif_3          Motif_3       Motif_3

NsTPS02a-Prom1kb   779 GTAATATTGCTACGACAGTTAGCAATTATAGCAAAAATGCTAAATCAGCTTTGTCGATTT
NsTPS02b-Prom1kb   769 GTAATATTGCTACGACAGTTAGCAATTATAGCAAAAATGCTAAATCAGCTTTGTCAATTT
NsTPS04-Prom1Kb    778 GTAATATTGCTACGACAGTTAGCAATTATAGCAAAAATGCTAAATTAGCTTTGTCAATTT
NsTPS03-Prom1kb    778 GTAATATTGCTACGACAGTTAGCAATTATAGCAAAAATGCTAAATTAGCTTTGTTAATTT
Consensus          778 GTAATATTGCTACGACAGTTAGCAATTATAGCAAAAATGCTAAATCAGCTTTGTCAATTT
                              Motif_1
```

FIGURE 1 (continued)

```
NsTPS02a-Prom1kb  839 AATITTGTAGCTAA.TTTTTTTATGAATTGTAAATAGCTATGAAATTTTAATTTTTGTG
NsTPS02b-Prom1kb  829 AATITTGTAGCTAA.TTTTTTTATGAAATTGTAAATAGCTATGAAATTTTAATTTTTGTG
NsTPS04-Prom1Kb   838 AATITTTTAGCTAAATTTTTTTATAAAATTGTAAATAGCCATGAAATTTTAATTTTTGTG
NsTPS03-Prom1kb   838 AATITTGTAGCTAAACTTTTTTAT.................GAAATTTTAATTTTTGTG
Consensus         838 AATITTGTAGCTAA.TTTTTTTATCAAATTGTAAATAGCTATCAAATTTTAATTTTTGTG
                           Motif_3

NsTPS02a-Prom1kb  898 GCTATTGTTAGGTATTAGCCACA..........TATAGCTAAGAATTTGTAGCTATATA
NsTPS02b-Prom1kb  888 GCTATTGTTAGGTATTAGCCACA..........TATAGCTAAGAATTTGTAGCTATATA
NsTPS04-Prom1Kb   898 GCTATTGTTAGGTATTAGCCACAATTTTCATATATGTATCTAAGAATTTGTAGCTATATA
NsTPS03-Prom1kb   880 GCTATTGATAGGTATTAGCTACAATTTTCATATATGTAGCTAAGAATTTGTAGCTATATA
Consensus         897 GCTATTGTTAGGTATTAGCCACA..........TATAGCTAAGAATTTGTAGCTATATA
                                                                    Motif_3

NsTPS02a-Prom1kb  947 TACATAATGTTGTAGTGGCAAATTCTAACATTGTAAGCTTGGCTGCCCTTTTTTTTTTTT
NsTPS02b-Prom1kb  937 TACATAATGTTGTAGTGGCAAATTCTAACATTGTACGCTTGGCTGCCCTTTTTTTTTTTT
NsTPS04-Prom1Kb   958 TACATAATGTTGTAGTGGCAAATTCTAACATTGTAAGCTTAGCTGCCCTTTTTTTTTTTT
NsTPS03-Prom1kb   940 TACATAATGTTGTAGTGGCAAATTCTAACATTGTACGCTTGGCTGCCCTTTTTTTTT...
Consensus         946 TACATAATGTTGTAGTGGCAAATTCTAACATTGTAAGCTTGGCTGCCCTTTTTTTTTTTT NsTPS02a-Prom1kb 1007 ......GGCTACAAAACTCTAAAGTAAAGGAACTAGAAAACTCGTTTGGCGAGAGAAAGA
NsTPS02b-Prom1kb  997 TT....GGCTACAAAACTCTAAAGTAAAGGAACTAGAAAACTCGTTTGGCGAGAGAAAGA
NsTPS04-Prom1Kb  1018 TTTTTTGGCTACAAAACTCTAAAGTAAAGGAACTAGAAAACTCGTTTGGCGAGAGAAAGA
NsTPS03-Prom1kb   997 ......GGCTACAAAACTCTAAAGTAAAGGAACTAGAAAACTCGTTTGGCGAGAGAAAGA
Consensus        1006 ......GGCTACAAAACTCTAAAGTAAAGGAACTAGAAAACTCGTTTGGCGAGAGAAAGA
                            Motif_3

NsTPS02a-Prom1kb 1061 GAGAG   ATG
NsTPS02b-Prom1kb 1053 GAGAG   ATG
NsTPS04-Prom1Kb  1078 GGGATCCATG
NsTPS03-Prom1kb  1051 GAGAGAGATG
Consensus        1060 GAGAG   ATG
```

FIGURE 1 (continued)

PLANT PROMOTERS AND USES THEREOF

CROSS-REFERENCE TO RELATED APPLICATION

This application is the U.S. national stage application of International Patent Application No. PCT/FR2005/002530, filed Oct. 12, 2005, the disclosure of which is hereby incorporated by reference in its entirety, including all figures, tables and amino acid or nucleic acid sequences.

The invention concerns tools, methods and compositions for modifying plants and/or protein expression in plants. The invention concerns in particular transcriptional promoters enabling specific expression in the trichomes, constructs containing said promoters, and their uses for genetically modifying cells, seeds or plants. The invention also concerns methods for producing transgenic plants expressing proteins or metabolites of interest. The invention is generally applicable to any plant having glandular trichomes, and to the expression of any protein of industrial interest, in particular therapeutic or phytosanitary.

INTRODUCTION

The surface of the leaves of certain higher plants (Angiosperms) contains organs called trichomes which, depending on their anatomy, are divided into two main types: non-secreting trichomes on the one hand and secreting trichomes on the other hand. The main function of glandular secreting trichomes is to secrete at the leaf surface resins and essential oils composed of a few major compounds.

In the tobacco plant, glandular secreting trichomes are composed of a foot made up of several (3-5) linearly arranged cells and a head containing a variable number (2-20) of secretory cells. Said cells primarily secrete sucrose esters and diterpenes. The latter account for up to 60% of the exudate and 10% of the dry weight of the adult plant (Wagner et al., 2004). In cultivated tobacco species (*Nicotiana tabacum*), the diterpenes produced belong to two separate families, the labdanes and the cembranes. The relative levels of production of the two families depend on the cultivar although cembrane production is generally four to ten times higher than labdane production. In *N. sylvestris*, a presumed progenitor of *N. tabacum*, labdanes are absent and a compound from the cembrane family, cembratriene-diol (CBT-diol), by itself accounts for more than 60% of the terpenes produced by the plant.

The steps leading to the biosynthesis of CBT-diol in tobacco have been partially elucidated and can be broken down into two different parts:
  Biosynthesis of the universal precursor of all diterpenes, geranylgeranyl pyrophosphate (GGPP), via the so-called "Rohmer" pathway (Rohmer et al., 1996), takes place in the chloroplast.
  Biosynthesis of CBT-diol from GGPP. Wang and Wagner (2003) have proposed the following biosynthetic pathway:

GGPP→CBT-ol→CBT-diol.

The first cyclization step would be carried out by an enzyme from a large family of enzymes known as terpene synthases (Bohlmann et al., 1998). The diterpene synthase of tobacco would use GGPP as substrate to form CBT-ol. The second step whereby CBT-diol is produced from CBT-ol is a hydroxylation catalyzed by an enzyme from the cytochrome P450 family. Professor G. Wagner's group (University of Kentucky) has used subtractive PCR to identify two *N. tabacum* candidate genes for each of these steps:
  a sequence displaying high homology with sequences coding for terpene synthases (CYC-2; Genbank No. AF401234. NID: AY495694).
  a sequence coding for a cytochrome P450-type enzyme (CYP71D16, NID: AF166332) (Wang et al., 2001, Wang & Wagner 2003).

Studies of the extinction of expression of these genes by co-suppression and RNA interference in *N. tabacum* have shown (i) a decrease in CBT-diol and CBT-ol correlated with a decrease in CYC-2 gene expression, and (ii) an increase in CBT-ol accumulation and a decrease in CBT-diol formation correlated with a decrease in CYC71D16 gene expression in the trichomes. These studies have suggested that (i) the CYC-2 gene codes for the CBT-ol cyclase responsible for CBT-ol synthesis and (ii) the CYP71D16 gene codes for a CBT-ol hydroxylase which converts CBT-ol to CBT-diol. Moreover, a genomic sequence of a gene very similar to CYC-2 mRNA has recently been deposited in the database (CYC-1, NID: AY049090), which suggests the existence of not one but several CBT-ol cyclase genes.

The expression of proteins in plants and/or the genetic modification of plants in order to confer them with particular properties is of major appeal, in both the phytosanitary and the pharmaceutical field. The availability of tools which can control or regulate the expression of genes in plants is therefore a key factor in the exploitation and development of said systems. In this regard, the development of promoters or other regulatory sequences specific of tissues, particularly of secreting trichomes, would be a very important advantage.

In this context, G. Wagner's group has shown that a 1852 bp regulatory sequence, located upstream of the ATG of the CYP71D16 gene, specifically directs the expression of the uidA reporter gene in the trichome secretory cells of tobacco (application US 2003/0100050 A1, Wagner et al., 2003). Furthermore, several promoter sequences extracted from different species have been shown to direct the expression of a heterologous gene in tobacco trichomes (Table 1).

Among said promoters, that of the LTP3 gene, coding for a cotton protein involved in lipid transfer (LTP), is specifically expressed in cotton fiber cells. The regulatory sequence of the gene (1548 bp) has been studied in tobacco. Said sequence specifically directs the expression of the uidA gene in leaf trichomes. The 315 bp sequence located between positions −614 and −300 upstream of the ATG is thought to underlie the promoter's specificity. The promoter of the LTP6 gene would also enable trichome-specific expression in cotton. Based on the literature, however, it would appear that the expression occurs in cells at the foot of the trichome, and not in the secretory cells. Moreover, when said promoters are introduced into tobacco, expression is no longer specific, with in particular a signal in epidermal cells (see Table 1).

Therefore, today, there is an important need for promoters or expression regulatory sequences, adapted to the expression of genes in plants, and enabling in particular a high and tissue-specific expression, in particular in secreting trichomes.

SUMMARY OF THE INVENTION

The application describes the identification and characterization of regulatory nucleic acid sequences of plant origin, which make it possible to specifically direct the expression of a gene of interest in the secretory cells of plant trichomes. Said promoters are easy to manipulate, of reasonable size, modulable, can be adapted to the expression of heterologous genes, and can drive expression specifically in certain plant tissues. Thus the application describes promoters, expression cassettes and vectors that can be used for modifying plants and expressing products of interest in plant tissues or cells.

A first object of the invention more particularly concerns a nucleic acid having functional transcriptional promoter activity in glandular trichomes, characterized in that it comprises a sequence selected in the group consisting of SEQ ID Nos. 1, 2, 3, 4 and 22, a fragment thereof having at least 100 consecutive bases or a functional variant thereof. More particularly, the nucleic acid comprises a sequence selected in the group consisting of SEQ ID Nos. 1, 2, 3, 4 and 22, and a fragment thereof having at least 100 consecutive bases or a sequence displaying at least 80% identity with one of said sequences, and is specific of glandular trichomes, in particular of the secretory cells of glandular trichomes.

Another object of the invention concerns a plant cell chloroplast transit peptide, comprising the sequence MSQSISPLMFSHFAKFQSNIWRCNTSQLRVIHSS-YASFGGRRKERVRRMNRAM DLSS (SEQ ID No. 10) or a functional fragment thereof, as well as a nucleic acid coding for one such peptide.

The invention also concerns any recombinant expression cassette comprising a gene of interest operatively linked to a nucleic acid such as defined hereinabove; any expression vector comprising a nucleic acid or a cassette such as defined hereinabove; and any modified cell comprising a cassette or a vector such as defined hereinabove. Preferably the cell is a plant cell, in particular from the family of Solanaceae, Asteraceae, Cannabaceae or Lamiaceae.

Another object of the invention concerns a method for producing a protein in the trichomes of a plant, comprising introducing into said plant a cassette or a vector such as defined hereinabove, comprising a gene coding for said protein.

Another object of the invention concerns a method for producing a protein in the trichomes of a plant, comprising introducing into a plant cell or seed a cassette or a vector such as defined hereinabove, comprising a gene coding for said protein, and regenerating a plant from said cell or seed.

Another object of the invention concerns a method for producing a plant expressing a recombinant protein, comprising introducing into a plant cell or seed a cassette or a vector such as defined hereinabove, comprising a gene coding for said protein, and regenerating a plant from said cell or seed. Advantageously, said protein is an enzyme whose activity in secretory cells leads to a modification of the composition of the exudate.

Another advantage consists in that the plant secretes the protein in the glandular trichome, and the protein is recovered from the exudate at the leaf surface.

Another object of the invention concerns any plant or seed comprising an expression cassette or a vector such as defined hereinabove.

The invention is also directed at the use of a nucleic acid such as defined hereinabove in order to specifically express a protein in the glandular trichomes of a plant. The invention also relates to kits comprising nucleic acids, vectors, cassettes and/or cells such as described earlier.

As described in detail hereinbelow, the invention is applicable to the expression of any gene of interest in any plant or plant tissue, preferably higher plants comprising glandular trichomes, for different applications, such as for the production of pharmaceutical or phytosanitary products of interest, or for the production of plants having improved or adapted properties.

DETAILED DESCRIPTION OF THE INVENTION

The present application describes the identification of plant trichome-specific promoters from the CBT-ol synthase genes of tobacco. Starting from the sequence of a cDNA coding for a terpene synthase, i.e. CBT-ol cyclase (CYC-2, NID: AF401234), four genes (named NsTPS-02a, 02b, 03, and 04) displaying strong sequence similarity to CYC-2 were identified from genomic DNA of the species *Nicotiana sylvestris*, using PCR methods.

An analysis of expression showed that said genes (in particular NsTPS-02a, 02b, and 03) are expressed in tobacco trichomes.

The promoter sequences, heretofore unknown, located upstream of the ATG of each of said four genes, have been identified and characterized. Each sequence is approximately 1 kb in size. The sequences are given in SEQ ID Nos. 1 to 4. Alignment of the four sequences reveals that they share more than 93% identity (FIG. 1, Table 2). In addition, said alignment reveals identical regions, most probably involved in the specificity of expression.

Construction of recombinant expression cassettes using said promoters has demonstrated, in an unexpected manner, an expression profile which is restricted and specific of trichome secretory cells. Such a profile was unexpected in so far as the expression characteristics of terpene synthases have not been documented at all in the prior art. Moreover, the results obtained by the applicants show that even the CYC-1 gene (NID: AY049090) whose genomic sequence was deposited by G. Wagner, is barely expressed in *N. tabacum* trichomes.

The present application therefore provides novel promoters, particularly advantageous for the expression of proteins in plants or plant tissues, in particular for specific expression in the cells of glandular trichomes. Said promoters are particularly advantageous since they enable the production of recombinant products directly in the exudate secreted by the leaves, thereby greatly facilitating the recovery of the recombinant products, if need be.

A particular object of the invention therefore concerns any nucleic acid having functional transcriptional promoter activity in glandular trichomes, characterized in that it comprises a sequence selected in the group consisting of SEQ ID Nos. 1, 2, 3, 4 and 22, a fragment thereof having at least 100 consecutive bases or a functional variant thereof (or of their complementary strand).

In a particular embodiment, the invention concerns any nucleic acid such as defined hereinabove, characterized in that it comprises a sequence selected in the group consisting of SEQ ID Nos. 1, 2, 3, 4 and 22, a fragment thereof having at least 100 consecutive bases or a sequence displaying at least 80% identity to one of said sequences, and in that it has transcriptional promoter activity specific of glandular trichomes.

In a specific embodiment of the invention, the nucleic acid comprises a sequence selected in the group consisting of SEQ ID Nos. 1, 2, 3, 4 and 22, preferably the sequence SEQ ID No. 2.

Figure 2A:
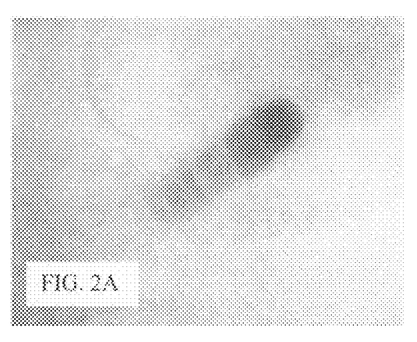
Figure 2B:
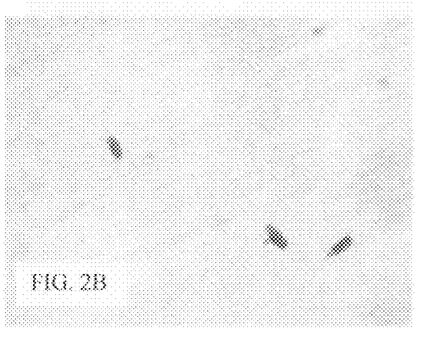
Figure 2C:
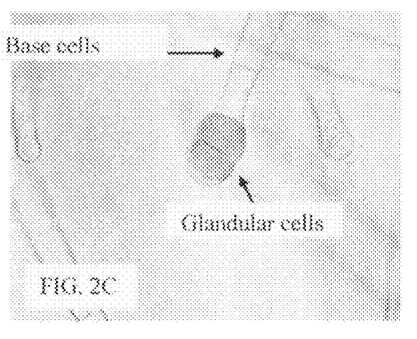
Figure 2D:
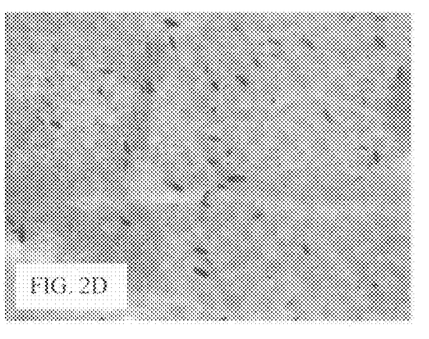

As illustrated in the examples, the 1065 base pair sequence of the TPS-02b gene promoter (SEQ ID No. 2) was cloned upstream of a uidA reporter gene (the sequence of the TPS02b promoter/uidA gene fusion is given by SEQ ID No. 5). Said construct (cassette No. 1) was inserted into a T-DNA vector (pBI121) containing a kanamycin resistance gene under the control of the nopaline synthase promoter of *Agrobacterium tumefasciens* (nos). Said T-DNA was introduced into *N. sylvestris* by genetic transformation using the strain *Agrobacterium tumefaciens* LBA4404 (Hoekema et al., 1993). UidA gene expression was detected in several transformants. The results in FIG. 2 show that expression was present in secretory cells, but not in the cells constituting the base of the trichomes. Furthermore, no uidA expression was detected in any of the other organs of the plant. These data indicate that the sequence under study can direct the expression of a heterologous gene in the secretory cells of glandular trichomes in a highly specific manner.

In the spirit of the invention, the term "nucleic acid" shall be understood to mean any molecule based on DNA or RNA. These can be molecules that are synthetic or semi-synthetic, recombinant, optionally amplified or cloned into vectors, chemically modified or containing non-natural bases. Typically they are isolated DNA molecules, synthesized by recombinant methods well known to those skilled in the art.

In the spirit of the invention, "specific" promoter shall be understood to mean a promoter mainly active in a given tissue or cell group. It shall be understood that a residual expression, generally lower, in other tissues or cells cannot be entirely excluded. For example, residual expression in other tissues or cells does not exceed 30% of the expression observed in glandular trichomes, preferably it does not exceed 20%, 10% or 5%. A particular feature of the invention is based on the ability to construct promoters specific of glandular trichome secretory cells, enabling a modification of the composition of the leaf secretions of the plant, and in particular enabling the expression therein of products of interest.

A nucleic acid "fragment" according to the invention advantageously refers to a fragment comprising at least 10 consecutive bases, more generally at least 20, 30, 40, 50, 60, 70, 80, 90 or 100. Nucleic acid "fragments" are typically fragments containing 100, 200, 300, 400 or 500 consecutive nucleotides of the sequence or more. Nucleic acid "fragments" are preferably fragments containing at least 100, 200, 300, 400 or 500 consecutive nucleotides of the sequence. Nucleic acid "fragments" can be used alone, or combined with other transcriptional regions, in order to construct chimeric promoters having a specificity for glandular trichomes. A promoter according to the invention is typically a region of the sequence displaying promoter activity.

FIG. 1 shows that the promoters according to the invention share a very high percentage of sequence identity with each other. In this regard, the analysis of said sequences allowed the inventors to identify parts thereof as conserved motifs necessary for specific expression in trichome secretory cells. Elimination of said motifs leads to a significant reduction in expression or a loss of specificity of expression. Said motifs, three in number, are defined by the following consensus sequences, where the letters K, W and Y represent nucleic acid bases according to the international nomenclature with K=G or T, W=A or T, and Y=C or T:

```
Motif 1: 5'-KKTCGTWGCAWT-3'    (SEQ ID No. 6)

Motif 2: 5'-AGTAATWTYW-3'      (SEQ ID No. 7)

Motif 3: 5'-TTGTAGCWAW-3'      (SEQ ID No. 8)
```

In a preferred embodiment, a fragment in the context of the invention comprises at least one sequence selected in the group consisting of SEQ ID No. 6, 7 or 8. Similarly, a particular object of the invention concerns any nucleic acid sequence comprising a sequence selected in the group consisting of SEQ ID No. 6, 7 or 8 or a functional variant thereof. Said nucleic acids are typically recombinant nucleic acids having transcriptional promoter activity. In particular they may be chimeric promoters, that is to say, comprising a sequence selected in the group consisting of SEQ ID No. 6, 7 or 8 or a functional variant thereof, operatively linked to a minimal promoter.

The term "functional variant" designates any nucleic acid bearing one or more modifications (that is to say for example a mutation, deletion, or addition of one or more bases) with respect to the parent sequences described herein, and conserving an activity, either of a transcriptional promoter, or a signal of expression specificity, or of transit. For example the functional variants can correspond to promoters derived from the corresponding genes of other plant species. For instance, the studies described in the examples herein concern sequences from the species Nicotiana sylvestris, one of the presumed diploid parents of cultivated tobacco, N. tabacum. It is known that the sequences of N. sylvestris and N. tabacum are extremely similar (up to 99% sequence identity between N. tabacum and N. sylvestris sequences), such that the promoters of the corresponding genes of N. tabacum constitute functional variants in the context of the invention, and can be easily prepared by conventional methods (hybridization, amplification, and the like). Other functional variants are nucleic acids, synthetic, recombinant or natural, whose sequence hybridizes, under conditions of high stringency, with one of the sequences SEQ ID No. 1, 2, 3, 4, 22 or a fragment having at least 100 consecutive nucleotides and which has transcriptional promoter activity, in particular specific of glandular trichomes.

In a general manner, functional variants are nucleic acids displaying at least 80, 85 or 90% identity with sequences SEQ ID No. 1, 2, 3, 4 or 22, or with the fragments thereof having at least 100 consecutive nucleotides, even more preferably more than 95% identity obtained by blastN sequence alignment software (Altschul et al., 1990).

The percentage of identity is determined by comparing two sequences which have been optimally aligned. The percentage of identity is calculated by determining the number of positions for which an identical residue appears in both sequences at the same position divided by the total number of positions and multiplied by 100. The optimal alignment of two sequences can be achieved for example with an algorithm to look for local homology (Smith & Watherman, 1981), or equivalent systems known to those skilled in the art.

The identified genes have also enabled the characterization of a transit peptide, which can target or direct a heterologous protein to the chloroplast compartment of plant cells, particularly trichomes. For instance, it is known that diterpene synthases have a peptide signal sequence at their N-terminal end required for their localization in the chloroplast compartment, the site of biosynthesis of geranylgeranyl pyrophosphate (GGPP) (Trapp and Croteau, 2001). By using the ChloroP program (Emanuelsson et al., 2000, Nielsen et al., 1997), a putative transit peptide of 51 amino acids (AA) was identified from the coding sequence of the TPS-02a gene. Said transit peptide (plus the following 6 AA) was introduced into cassette No. 1, upstream of the uidA gene and downstream from the TPS-02b promoter. In this manner a translational fusion of the transit peptide with the GUS protein was produced. Said construct (cassette No. 2) was inserted into a T-DNA vector (pBI121) carrying a kanamycin resistance gene under the control of the cauliflower mosaic virus promoter (CaMV 35S). This T-DNA was introduced into N. sylvestris by genetic transformation using the strain Agrobacterium tumefaciens LBA4404 (Hoekema et al., 1993).

As for cassette No. 1, uidA gene expression in several transformants was only detected in glandular trichome secretory cells. Furthermore, microscopic examination showed that GUS activity was located in plasts, indicating that the GUS protein was correctly targeted to the chloroplast compartment. These data demonstrate that the sequence under study, corresponding to the CBT-ol cyclase transit peptide of

*N. sylvestris*(TPS-02b), directs the localization of a heterologous protein to the chloroplast compartment.

Another object of the invention therefore concerns a plant cell chloroplast transit peptide, comprising the following amino acid sequence MSQSISPLMFSHFAKFQSNIWRCNTSQLRVIHSSYASFGGRRKERVRRMNRAMDLSS (SEQ ID No. 10) or any fragment or functional variant thereof, as well as a nucleic acid coding for a plant cell chloroplast transit peptide, comprising the nucleotide sequence: "ATGAGTCAATCAATTTCTCCATTAATGTTTTCTCACTTTGCAAAATTTCAGT CGAATATTTGGAGATGCAATACTTCTCAACTCAGAGTTATACACTCATCATATGCCTCTTTTGGAGGGAGAAGAAAAGAGAGAGTAAGAAGAATGAATCGAG CAATGGATCTTTCTTCA" (SEQ ID No. 9), or any fragment or functional variant thereof.

The invention also relates to any recombinant expression cassette, characterized in that it comprises a gene and/or a promoter of interest operatively linked to a nucleic acid such as defined hereinabove.

The term expression cassette designates a nucleic acid construct comprising a coding region and a regulatory region, operatively linked. The expression "operatively linked" indicates that the elements are combined in such a way that the expression of the coding sequence (the gene of interest) and/or the targeting of the coded protein are under control of the transcriptional promoter and/or the transit peptide. Typically, the promoter sequence is placed upstream of the gene of interest, at a distance therefrom which is compatible with control of expression. Likewise, the sequence of the transit peptide is generally fused upstream of the sequence of the gene of interest, and in frame with it, and downstream of any promoter. Spacer sequences may be present, between the regulatory elements and the gene, as long as they do not prevent expression and/or targeting.

The gene of interest can be any nucleic acid (for example a DNA or RNA) containing a region coding for an expression product (for example a mRNA or a protein). In a preferred embodiment, the gene of interest codes for a therapeutic or phytosanitary protein, an enzyme, a resistance protein, a transcriptional activator or a viral genome.

Another object of the invention relates to any (expression) vector comprising a nucleic acid or a cassette such as defined hereinabove. The vector can be DNA or RNA, circular or not, single- or double-stranded. Typically it is a plasmid, phage, virus, cosmid, artificial chromosome, etc. Advantageously it is a plant vector, that is to say, capable of transforming a plant cell. Examples of plant vectors are described in the literature, among which one can cite in particular the *A. tumefaciens* T-DNA plasmids pBIN19 (Bevan, 1984), pPZP100 (Hajdukewicz et al., 1994), pCAMBIA series (R. Jefferson, CAMBIA, Australia). The vectors of the invention can additionally comprise an origin of replication and/or a selection gene and/or a plant recombination sequence, etc. The vectors can be constructed by conventional molecular biology methods, well known to those skilled in the art, using for example restriction enzymes, ligation, clonings, replication, etc. Specific examples of vectors according to the invention are provided in the experimental section, and include in particular pLIBRO-01 and pLIBRO-02.

The gene constructs of the invention can be used to genetically modify plants, and in particular to introduce and express proteins in plant tissues, including whole plants.

Introduction of the inventive constructs into a plant cell or tissue, including a seed or plant, can be carried out by any method known to those skilled in the art. Plant transgenesis methods are well known in the field, and comprise for example the use of the bacterium *Agrobacterium tumefaciens*, electroporation, conjugative transfer, gene gun methods, and the like.

A commonly used method is based on the use of the bacterium *Agrobacterium tumefaciens*, which mainly consists in introducing the construct of interest (nucleic acid, cassette, vector, etc.) in the bacterium *A. tumefaciens*, then contacting said bacterium with the leaf disks of the chosen plant. The expression cassette is typically introduced in the bacterium by using as vector the Ti plasmid (or T-DNA), which can be transferred into the bacterium for example by heat shock. Incubation of the transformed bacteria with leaf disks leads to transfer of the Ti plasmid into the genome of the disk cells. The latter can optionally be cultivated in suitable conditions in order to regenerate a transgenic plant, the cells of which comprise the construct of the invention. For further details or variant implementations of the *A. tumefaciens* transformation method, reference can be made to Horsch et al., 1985 or Hooykaas and Schilperoort, 1992 for example.

Another method of plant transformation is based on projecting microparticles (typically microbeads) to which gene constructs are attached, directly on plant cells, then culturing said cells in order to regenerate a transgenic plant. The particles which are used are typically gold particles, which are typically projected by means of a particle gun (see in particular Russell et al., In Vitro Cell. Dev. Biol., 1992, 28P, p. 97-105).

The microinjection method is based primarily on injecting the gene constructs into plant protoplasts or embryos, then cultivating said tissues so as to regenerate whole plants. Other plant transgenesis methods are well known, or other protocols implementing the above methods are described in the prior art (Siemens, J and Schieder, 1996) and can be employed in the invention.

Once regenerated, the transgenic plants can be tested for expression of the product of interest in the trichomes. This can be done by collecting the leaf exudate and testing for the presence of the product in said exudate, when the product is meant to be secreted. This can also be done by analyzing the presence of the expression product of the gene of interest in the leaves and, more particular, in the trichome cells (for example by analyzing mRNA or genomic DNA with specific primers or probes). Optionally the plants can be selected, crossed, treated, etc. in order to obtain plants displaying improved levels of expression.

In this regard, another object of the invention concerns a recombinant cell comprising a cassette or a vector such as defined hereinabove. For example it can be a plant cell, in particular from the Solanaceae, Asteraceae, Cannabaceae or Lamiaceae family. The cells can be cultivated in vitro, and used to regenerate tissues or whole plants, in order to produce proteins in culture, or else to study the properties of genes or proteins of interest (for example by functional genomics).

Another object of the invention also concerns a plant or seed comprising an expression cassette or a vector such as defined hereinabove.

The invention further concerns a method for producing a protein in a plant, in particular in the glandular trichome of a plant, comprising introducing into said plant a cassette or a vector such as defined hereinabove, comprising a gene coding for said protein.

Another aspect of the invention concerns a method for producing a protein in a plant, in particular in the glandular trichome of a plant, comprising introducing into a plant cell or seed a cassette or a vector such as defined hereinabove, comprising a gene coding for said protein, and regenerating a plant from said cell or seed.

The invention also concerns any method for producing a plant expressing a recombinant protein, comprising introducing into a plant cell or seed a cassette or a vector such as defined hereinabove, comprising a gene coding for said protein, and regenerating a plant from said cell or seed.

Advantageously, the recombinant protein expressed in the trichome leads to the production by the secretory cells of a molecule secreted in the leaf surface exudate and/or to a modification of the exudate composition.

Advantageously, the plant secretes the protein in the glandular trichome, and the protein is recovered in the exudate at the leaf surface.

The invention can thus be used to modify plants, plant cells or tissues, in order to make them express different products of interest.

The invention can be used in particular to express products of interest specifically in the secretory cells of glandular trichomes of higher plants (in particular Angiosperms). The invention can be applied in particular to any plants from families having glandular trichomes, for example Asteraceae, Solanaceae, Cannabaceae and Lamiaceae. The invention is particularly adapted to plants from the Solanaceae family, such as for example the genuses Solanum, Lycopersicon, Capsicum, Petunia, Datura, Atropa, etc., and to Nicotianae, for example *Nicotiana sylvestris* and *N. tabacum*.

The product of interest can be any recombinant protein, including peptides, enzymes, antibodies, and the like. In particular it can be a protein having a biological activity of industrial interest, for example medical or phytosanitary. It can also be a protein intended to confer particular properties to the plant (in particular a modification of the composition of the secretion (exudate)), such as resistance to pathogens (destructive insects, fungi, bacteria, viruses, etc.), improved growth, a modified metabolite content or a modified synthetic pathway, etc.

The invention can also be used in order to express, in a plant cell or a plant, a transcriptional activator. In this case, the transcriptional activator produced will enable control of the expression of a protein of interest placed under control of a promoter responding to said activator. Such a binary system, using two cassettes (present on a same vector or on different vectors) makes it possible to amplify the specific expression obtained with the aid of the invention. One such example is a system comprising a first cassette containing the gene coding for a transcriptional activator (for example GAL4) under the control of the trichome-specific promoter, and another cassette comprising the gene coding for the protein of interest under the control of elements known to be regulated by the transcription factor (Gal4).

Another amplification system consists in the use of a viral RNA vector. In fact, some plant RNA viruses code for an RNA-dependent RNA polymerase which allows amplification of the transcripts of a given gene. In this embodiment, the gene of interest is cloned downstream from the promoter of said RNA polymerase, in place of the open reading frame coding for the viral coat protein. The virus is itself placed under the control of the specific promoter. Expression of the virus is therefore restricted to trichome secretory cells, thereby allowing selective amplification of expression of the gene in said cells.

Other aspects and advantages of the invention will become apparent in the following examples, which are given for purposes of illustration and not by way of limitation.

LEGENDS OF FIGURES

FIG. 1: Alignment of promoter sequences of the invention: The sequences of the four TPS promoters (NsTPSO2a, SEQ ID NO:1; NsTPSO2b, SEQ ID NO:2; NsTPS03, SEQ ID NO:3; and NsTPSO4. SEQ ID NO:4) approximately 1 kb in length were aligned with the AlignX alignment program (VectorNTI suite, INFORMAXINC). Motifs required for specific trichome activity are shaded in gray.

FIG. 2: Visualization under a microscope (A and B) and a low-power stereo microscope (B and D) of trichome glandular cells of different organs after histochemical staining of the tissues with X-Gluc. UidA reporter gene expression, stained in blue, is detected only in trichome glandular cells. The cells at the base of the trichome are not stained. Staining was carried out on two tobacco lines transformed with the pLI-BRO-01 construct. A and C: leaf trichomes, B: stalk trichomes, D: sepal trichomes.

EXAMPLES

1. Sequence Isolation and Characterization

Genomic DNA was extracted from tobacco leaves (*N. sylvestris* or *N. tabacum*) with the aid of a Qiagen® commercial kit (DNeasy Plant Maxi Kit). The promoter regions of the different TPS genes (TPS02a, 02b, 03, and 04) were cloned by using the "adapter-anchor" PCR method (Siebert et al., 1995). Briefly, genomic DNA was digested separately with different restriction enzymes generating blunt ends (DraI, SspI, NaeI . . . ) and ligated to an adapter composed of the following primers: ADPR1 5'-CTAATACGACTCACTAT-AGGGCTCGAGCGGCCGCCCGGGGAGGT (SEQ ID No. 14) and ADPR2 5'-ACCTCCCC (SEQ ID No. 15). The TPS-02 gene promoter region was then identified by successively carrying out two PCR reactions (PCR1 followed by PCR2) with primers complementary to the adapter (AP1 and AP2) and different primers of the published CYC-2 gene coding sequence (Genbank No. AF401234, NID: AY495694). To identify promoter sequences of approximately 1 kb, the PCR1 reaction was carried out with the AP1 primer (5'-GGATC-CTAATACGACTCACTATAGGGC, SEQ ID No. 16) and the external primer 2A04 (5'-AGAGGCATATGATGAGTG-TATAACTC, SEQ ID No. 17). An aliquot of the PCR1 reaction was used to carry out the PCR2 reaction with the AP2 primer (5'-CTATAGGGCTCGAGCGGC, SEQ ID No. 18) and the internal primer 2A02 (5'-ACCTCCAAATATTC-GACTGAAATTT, SEQ ID No. 19). The fragments obtained by this method ranged in size from 200 to 1000 bp. In order to isolate the largest sequences, the same process was repeated on the newly identified sequences. For example, to identify the 1.7 kb promoter sequence corresponding to the TPS-02b gene, the PCR1 reaction was carried out on the same genomic material and in the same PCR conditions but using the external primer 2G07 (5'-GTCATGTGCTTGAAGTTAC-CATATC, SEQ ID No. 20) and the internal primer 2G08 (5'-GTTACCATATCAATATTATTTACCAT, SEQ ID No. 21). The PCR amplifications were all carried out in the same standard PCR conditions with 0.25 unit Taq polymerase (supplier: Eppendorf) in 25 µl of reaction mixture in the following conditions: 1 cycle at 94° C. 2 min, then 35 cycles at 94° C. 30 sec, 68° C. 30 sec and 1 cycle at 72° C. 5 min using 50 ng of genomic DNA.

To clone the TPS-02b promoter (PromTPS02b) in the binary vector, another PCR amplification was carried out on genomic DNA using the sense primer, 3A04 (sequence 5'-CT AAGCTTAATTTATTTTTGTAAAACTTC, SEQ ID No. 11)

which has a 5' HindIII site and the antisense primer, 3A03 (sequence 5'-ATGGATCCCTCTTTCTCTCGCCA AACGAGT, SEQ ID No. 12) which has a 5' BamH1 site. To clone the TPS-02b promoter comprising the transit peptide (promTPS02b-TP), the sense primer 3A04 was used with the antisense primer 4C01 (5'-TGGATCCTGAAGAAAGATC-CATTGCTCGA, SEQ ID No. 13), comprising a 5' HindIII site. To clone the TPS-02b__1.7 kb promoter (PromTPS02b__1.7, SEQ ID No. 22), the sense primer 4E07 which has a 5' SacI site (5' TGAGCTCAAAGAGGTGAAAC-CTAATCTAGTATGCAA 3', SEQ ID No. 23) was used with the primer 3A03. The amplifications were carried out with Taq polymerase (Eppendorf®) in the following conditions: 1 cycle at 94° C. 2 min, 35 cycles at 94° C. 30 sec, 57° C. 30 sec, 72° C. 1 min and 1 cycle at 72° C. 5 min using 50 ng of genomic DNA in a 25 µl reaction. The PCR products were purified on a Qiaquick column (Qiagen) and cloned into the pGEM-T vector (Promega®) to yield plasmids pPromTPS02b and pPromTPS02b-TP, respectively. The clones were sequenced, and the sequences of the 1 kb promoter regions are represented by SEQ ID Nos. 1 to 4. Alignment of the sequences (FIG. 1) revealed 93% identity or higher. Alignment with the 1.7 kb sequences gave sequence identities greater than 90%.

2. Construction of Transformation Vectors and Cassettes

The CaMV 35S promoter located upstream of the uidA gene in the binary vector pBI121 (AF485783) was removed by HindIII and BamH1 enzymatic digestion and purified on an agarose gel on a Qiaquick column (Qiagen®). The PromTPS02b and PromTPS02b-TP promoter sequences were purified on a Qiaquick column (Qiagen®) after HindIII and BamH1 digestion of plasmids pPromTPS02b and pPromTPS02b-TP. The promoter sequences were inserted into the HindIII and BamH1 sites of the pBI121 vector by replacing the CaMV 35S promoter thereby creating a transcriptional fusion with the uidA gene, to yield constructs respectively named pLIBRO-18 and pLIBRO-19. The two binary vectors pLIBRO-01 and 02 were introduced into *Agrobacterium* strain LBA4404 by electroporation.

The promTPS02b__1.7 promoter was cloned into the EcoRI site of the vector pCAMBIA1391Z (NID: AF234312) to yield vector pLIBRO-32.

3. Genetic Transformation

Transgenic tobacco lines (*N. sylvestris*) carrying the pLIBRO-01, pLIBRO-02 and pLIBRO-32 constructs were obtained by genetic transformation with the corresponding *Agrobacterium* strains by using the leaf disk method (Horsch et al., 1985). Transformants were selected with 100 mg/l kanamycin sulfate and *Agrobacterium* was eliminated with 250 mg/l carbenicillin.

4. Analysis of uidA Gene Expression

UidA gene expression was detected by the histochemical GUS assay as described by Jefferson et al. (1987). A low power stereo microscope was used to visualize the staining.

5. Demonstration of Specific Expression in Trichromes

UidA gene expression was measured in several transgenic tobacco lines (*N. sylvestris*) carrying the pLIBRO-01 and pLIBRO-32 construct. The results for the pLIBRO-01 construct are presented in FIG. 2 (see legend above).

The data show that expression occurred in secretory cells, but not in the cells forming the base of the trichomes. Furthermore, no uidA gene expression was detected in other organs of the plant. These results demonstrate that the test sequence directs the expression of a heterologous gene in secretory cells of glandular trichomes in a highly specific manner. Identical results were obtained with the pLIBRO-32 construct (data not shown).

6. Demonstration of Chloroplast Targeting

UidA gene was measured in several transgenic tobacco lines (*N. sylvestris*) carrying the pLIBRO-02 construct.

As for cassette No. 1, uidA gene expression in several transformants was detected only in glandular trichome secretory cells. Furthermore, under the microscope, GUS activity was found to be localized in chloroplast cells, indicating that the GUS protein was correctly targeted to the chloroplast compartment. These results show that the transit peptide sequence of the invention targets a heterologous protein to the chloroplast compartment.

TABLE 1

| Gene abbreviation | Name of gene | Plant | Promoter (bp) | Plant transformed | Expression | References |
|---|---|---|---|---|---|---|
| LTP3 | Lipid transfer protein | Cotton | 1548 1143 614 | Tobacco | Trichomes, peripheral epidermis of leaves and vascular tissues | Liu et al., 2000, BBA, 1487: 106111 |
| LTP6 | Lipid transfer protein | Cotton | 447 272 | Tobacco | Trichomes and stomate guard cells | Hsu et al., 1999, Plant Science, 143: 6370 |
| wax9D | Lipid transfer protein | *Brassica oleracea* | 972 | Tobacco | Epidermis of leaf, stems and flowers, petals, sepals, ovules, and trichomes | Pyee and Kolattukudy, 1995, Plant J. 7: 4559 |
| LTP1 | Lipid transfer protein | *Arabidopsis* | 1149 | *Arabidopsis* | Epidermal cells from various tissues | Thoma et al., 1994, Plant Physiol. 105 3545 |
| CYC71D16 | CBT-ol hydroxylase | Tobacco | 1852 | Tobacco | Trichomes | Wang et al., 2002, J. Exp. Bot. 1891-1897 |

TABLE 2

| | NsTPS02a-Prom1kb | NsTPS02b-Prom1kb | NsTPS03-Prom1kb | NsTPS04-Prom1Kb |
|---|---|---|---|---|
| NsTPS02a-Prom1kb | 100 | 96 | 93 | 94 |

TABLE 2-continued

|  | NsTPS02a-Prom1kb | NsTPS02b-Prom1kb | NsTPS03-Prom1kb | NsTPS04-Prom1Kb |
|---|---|---|---|---|
| NsTPS02b-Prom1kb |  | 100 | 93 | 93 |
| NsTPS03-Prom1kb |  |  | 100 | 93 |
| NsTPS04-Prom1Kb |  |  |  | 100 |

REFERENCES

Altschul S F, Gish W, Miller W, Myers E W, Lipman, D J (1990) J. Mol. Biol. 215:403-410.
Bevan M (1984) Nucl. Acids Res. 12:8711-8721.
Bohlmann J, Meyer-Gauen G, Croteau R (1998) Proc. Natl. Acad. Sci. USA 95:4126-4133.
Emanuelsson O, Nielsen H, Brunak S and Von Heijne G (2000) J. Mol. Biol. 300:1005-1016.
Jefferson R A. (1987) Plant Mol. Biol. Rep. 5:387-405.
Hajdukiewicz P, Svab Z, Maliga P (1994) Plant Mol. Biol. 25:989-994.
Nielsen H, Engelbrecht J, Brunak S, and Von Heijne G (1997) Prot. Eng. 10:1-6.
Hoekema A, Hirsch P R, Hooykaas P J J and Schilperoort R A (1983) Nature 303:179-180.
Hooykaas P J J and Schilperoort R A (1992) Plant Mol. Biol. 19:15-38.
Horsch R B, Fry J, Hoffmann N L, Wallroth M, Eichholtz D, Rogers S G, and Fraley R T (1985) Science 227:1229-1231.
Rohmer M, Seeman M, Horbach S, Bringer-Meryer S, and Sahm H (1996) J. Am. Chem. Soc. 118:2564-2566.
Siebert P D, Chenchick A, Kellogg D E, Lukyanov K A, Lukyanov S A (1995) Nucl. Acids Res. 23:1087-1088.
Siemens J, and Schieder A (1996) Plant Tiss. Cult. Biotechnol. 2:66-75.
Smith T F, and Watherman M S (1981) Add. Appl. Math. 2:482.
Trapp S C, and Croteau R B (2001) Genetics 158:811-832.
Wagner G J, Gan S, Wang E, Wang R. (2003) US patent 2003/0100050-A1.
Wagner G J, Wang E, Shepherd R W (2004) Ann. Botany 93:3-11.
Wang E, Wang R, DeParasis J, Loughrin J, Gan S, and Wagner G J (2001) Nature 19:371-374.
Wang E, Gan S, and Wagner G J (2002) J. Exp. 53:1891-1897.
Wang E and Wagner G J (2003) Planta 216:686-691.

The invention claimed is:

1. A composition of matter comprising:
   a) recombinant expression cassette comprising a heterologous gene of interest operatively linked to a nucleic acid comprising:
      (i) SEQ ID NO: 22; or
      (ii) SEQ ID NO: 1;
   b) an expression vector comprising a heterologous gene of interest operatively linked to a nucleic acid comprising:
      (i) SEQ ID NO: 22; or
      (ii) SEQ ID NO: 1;
   c) an isolated recombinant cell comprising a recombinant expression cassette, said recombinant expression cassette comprising a heterologous gene of interest operatively linked to a nucleic acid comprising:
      (i) SEQ ID NO: 22; or
      (ii) SEQ ID NO: 1;
   or
   d) a transgenic plant or transgenic seed comprising a recombinant expression cassette, said recombinant expression cassette comprising a heterologous gene of interest operatively linked to a nucleic acid comprising:
      (i) SEQ ID NO: 22; or
      (ii) SEQ ID NO: 1.

2. The composition of matter according to claim 1, wherein said expression cassette comprises a heterologous gene of interest that encodes an enzyme leading to the modification of the composition of the exudate secreted by the trichomes.

3. The composition of matter according to claim 1, wherein said expression cassette comprises a heterologous gene of interest that encodes a therapeutic or phytosanitary protein, an enzyme, a resistance protein, a transcriptional activator or a viral genome.

4. The composition of matter according to claim 1, wherein said expression cassette further comprises a nucleic acid encoding SEQ ID NO: 10.

5. The composition of matter according to claim 1, wherein said recombinant cell is a plant cell.

6. The composition of matter according to claim 5, wherein said plant cell is from the family Solanaceae, Asteraceae, Cannabaceae or Lamiaceae.

7. A method for producing a protein in a plant comprising introducing into a plant cell or seed a recombinant cassette comprising a gene of interest that encodes a protein of interest and regenerating a plant from said plant cell or seed that produces said protein of interest, said recombinant expression cassette comprising a heterologous gene of interest operatively linked to a nucleic acid comprising:

(i) SEQ ID NO: 22; or
(ii) SEQ ID NO: 1.

8. The method according to claim 7, further comprising recovering the protein of interest from exudate at the leaf surface.

9. The method according to claim 7, wherein the plant, plant seed or plant cell is from the family Solanaceae, Asteraceae, Cannabaceae or Lamiaceae.

10. The composition of matter according to claim 1, wherein said expression vector comprises a heterologous gene of interest operatively linked to a nucleic acid that comprises SEQ ID NO: 1.

11. The composition of matter according to claim 1, wherein said expression vector comprises a heterologous gene of interest operatively linked to a nucleic acid that comprises SEQ ID NO: 22.

12. The composition of matter according to claim 1, wherein said transgenic plant or transgenic seed is from the family Solanaceae, Asteraceae, Cannabaceae or Lamiaceae.

13. The composition of matter according to claim 1, wherein said composition of matter comprises a recombinant expression cassette comprising a heterologous gene of interest operatively linked to a nucleic acid comprising SEQ ID NO: 22.

14. The composition of matter according to claim 1, wherein said composition of matter comprises a recombinant expression cassette comprising a heterologous gene of interest operatively linked to a nucleic acid comprising SEQ ID NO: 1.

15. The composition of matter according to claim 1, wherein said composition of matter comprises an isolated recombinant cell comprising a recombinant expression cassette, said recombinant expression cassette comprising a heterologous gene of interest operatively linked to a nucleic acid comprising SEQ ID NO: 22.

16. The composition of matter according to claim 1, wherein said composition of matter comprises an isolated recombinant cell comprising a recombinant expression cassette, said recombinant expression cassette comprising a heterologous gene of interest operatively linked to a nucleic acid comprising SEQ ID NO: 1.

17. The composition of matter according to claim 1, wherein said composition of matter comprises a transgenic plant or transgenic seed comprising a recombinant expression cassette, said recombinant expression cassette comprising a heterologous gene of interest operatively linked to a nucleic acid comprising SEQ ID NO: 22.

18. The composition of matter according to claim 1, wherein said composition of matter comprises a transgenic plant or transgenic seed comprising a recombinant expression cassette, said recombinant expression cassette comprising a heterologous gene of interest operatively linked to a nucleic acid comprising SEQ ID NO: 1.

19. The composition of matter according to claim 17, wherein said composition of matter is a transgenic plant.

20. The composition of matter according to claim 17, wherein said composition of matter is a transgenic seed.

21. The composition of matter according to claim 18, wherein said composition of matter is a transgenic plant.

22. The composition of matter according to claim 18, wherein said composition of matter is a transgenic seed.

* * * * *

SEQUENCE LISTING

```
<160> NUMBER OF SEQ ID NOS: 23

<210> SEQ ID NO 1
<211> LENGTH: 1068
<212> TYPE: DNA
<213> ORGANISM: Nicotiana sylvestris

<400> SEQUENCE: 1
aatttatttt cataaaactt ctctaatttt tgaacaaaat cttatattga tttttttaatc      60 aaagccaaaa tatttattta actatgaaaa ttttttaaca actaatttat tatggtaaat     120
aatattgata tggtaacttc aagcacatga caaaaattat aactaactgc agaagtttac     180
tgtctctctg aatcttgtgg ctatgtcatt ctatcataac aaatacttgt agctaatacg     240
ccaacgatgt tctcgatttc atataatttg aattttaaaa tagcttttaa atttaatatt     300
tatttcaaat cattattgtg actaacatgt tataaccgca gtaatatttg gagatgcaat     360
acttatattt agctacaaaa ttttattgta tcataataag tttgtagcta ttaagttagt     420
ttttgccaca aatttttata attgaagcaa aaatacctat tcaactacaa tattttgtat     480
cgagtaatat tttgtgacta gaagattaat attattacag taatttcaga cgtgtggcaa     540
aaactcataa ttatctacaa aatattgtcg tagcaataat tttttatatc tattaatcca     600
attattgcta catgctttta taacttgagg caaaaatatc tatttagcta taacattttg     660
ttagaagtaa tttttgtgac tataaagttg ttattgctac agtaatttca aatgcgtggc     720
aaaaaaaata cgattagcta cgaaatttta ttgtagcaat aaatttgtag ctatttgggt     780
aatattgcta cgacagttag caattatagc aaaaatgcta aatcagcttt gtcgatttaa     840
ttttgtagct aattttttta tgaatttgta aatagctatg aaatttttaat ttttgtggct     900 attgttaggt attagccaca tatagctaag aatttgtagc tatatataca taatgttgta     960
gtggcaaatt ctaacattgt aagcttggct gccttttttt tttttggct acaaaactct    1020 aaagtaaagg aactagaaaa ctcgtttggc gagagaaaga gagagatg                 1068
```

<210> SEQ ID NO 2
<211> LENGTH: 1060
<212> TYPE: DNA
<213> ORGANISM: Nicotiana sylvestris

<400> SEQUENCE: 2

```
aatttatttt tgtaaaactt ctctaatttt tggacaaact cttatattga ttttttaatc      60
aaagccaaaa tatttattta actatgaaaa aattttaaca actaatttat tatggtaaat     120
aatattgata tggtaacttc aagcacatga caaaaattat aactaactgc agaagtttat     180
tgtctctctg aatcttgtgg ctatatcata acaaatactt gtagctaata agccaacgat     240
gttctcggtt tcatataatt tgaattttaa aatagttttt aaatttaata tttatttcaa     300
atcattattg tggctaacat gttataatcg cagtaatatt tggagatgca atacttatat     360
ttagctacaa aattttattg tatcagaata agtttgtagc tattaagtta gttttgcca      420
caaattttta taattgaagc aaaaatactt attcagctac agtatttgt atcgagtaat      480
attttgtgac tagaagatta atattgctac agtaatttca gacgtgtggc aaaaactcat     540
aattagctac aaaatattgt cgtagcaata attttttata tctattaatg caattattac     600
tacatgcttt taaacttga ggcaaaaata tctaatagct ataacatttt gttagaagta     660
attttgtgg ctataaaatt ggtattgcta cagtaatttc aaatgcgtgg caaaaaaata     720
cgattaacta cgaaatttta ttgtagcaat aactttgtag ctatttgggt aatattgcta     780
cgacagttag caattatagc aaaaatgcta atcagctttt gtcaatttaa ttttgtagct     840
aattttttta tgaaattgta aatagctatg aaatttaat ttttgtggct attgttaggt      900
attagccaca tatagctaag aatttgtagc tatatataca taatgttgta gtggcaaatt     960
ctaacattgt acgcttggct gccctttttt ttttttttgg ctacaaaact ctaaagtaaa    1020
ggaactagaa aactcgtttg gcgagagaaa gagagagatg                          1060
```

<210> SEQ ID NO 3
<211> LENGTH: 1060
<212> TYPE: DNA
<213> ORGANISM: Nicotiana sylvestris

<400> SEQUENCE: 3

```
aatttatttt cgtaaaattt ctctaatttg gacaaactct tatattgatt ttttaatca      60
aagccaaaat atttatttaa ctatgaaaat ttttaacaa ctaatttatt atggtaaata     120
atattgatat ggtaacttca agcacatgat aaaaattata actaactgca gaagtttact    180
gtctctttga atcttgtggt tatatcattc tatcataaca atacttgta gctaataagc      240
caacgatgtt ctcggtttca tataatttga attttaaaat agtttttaaa tttaatattt     300
atttcaaatt attattgtgg ctaacatgtt ataaccgcag taatatttgg agatgcaata     360
cttatattta gcttgaaaat tttattgtat cagaacaagt ttgtagctat aagttagtt     420
tttgccacaa attttataa ttgaagcaaa ataccctatt cagctacagt attttgtatc     480
gagtaatatt ttgtgactag aagattaata ttgctacagt aatttcagac gtgtggcaaa    540
aactcataat tagctacaaa atattgtcgt agcaataatt ttttatatct attaatccaa    600
ttattgctac atgcttttat aacttgaggc aaaaatatct atttagctat aacatttat     660
taaaagtaat ttttgtggct ataaagttgt tattgctaca gtaatttcaa atgcgtggca    720
aaaaaaatac gattagctac gaaattttat tgtagcaata aatttgtagc tatttgggta    780
atattgctac gacagttagc aattatagca aaaatgctaa attagctttg ttaatttaat    840
```

| | |
|---|---|
| tttgtagcta aacttttttta tgaaatttta attttttgtgg ctattgatag gtattagcta | 900 |
| caattttcat atatgtagct aagaatttgt agctatatat acataatgtt gtagtggcaa | 960 |
| attctaacat tgtacgcttg gctgcccttt tttttttggct acaaaactct aaagtaaagg | 1020 |
| aactagaaaa ctcgtttggc gagagaaaga gagagagatg | 1060 |

<210> SEQ ID NO 4
<211> LENGTH: 1087
<212> TYPE: DNA
<213> ORGANISM: Nicotiana sylvestris

<400> SEQUENCE: 4

| | |
|---|---|
| aatttatttt cgtaaaattt ctctaatttt tggacaaact cttatattgg ttttttaatc | 60 |
| aaagccaaaa tatttattta actatgaaat tttgttgaac aactaattta ttatggtaaa | 120 |
| taatattgat atggtaactt caagcacatg acaaaaatta taactaactg cagaagttta | 180 |
| ctgtctctct gaatcttgtg ctatatcat tctatataac aaatacttgt agctaataag | 240 |
| ccaacgatgt tctcggtttc ataaatttg aattttaaaa tagttttaa atttaatatt | 300 |
| tatttcaaat cattattgtg gctagcatgt tataaccgca gtaatatttg gagatgcaat | 360 |
| acttatattt agctacaaaa ttttattgta tcagaataag tttgtaacta ttaagttagt | 420 |
| ttttgccaca aattttata attgaagcaa aaatacctat tcagctacga tattttgtat | 480 |
| cgagtaatat tttgtgacta gaagattaat attgctagag taatttcaga cgtgtggcaa | 540 |
| aaactcataa ttagctacaa aatattgtcg tagcaataat tgtttatatc tattaatcca | 600 |
| attattgcta tatgcttta taacttgagg caaaaatatt tatttagcta taacattttg | 660 |
| ttagaagtaa ttttgtggc tataaagttg ttattgctac ggtaatttca aatgcgtggc | 720 |
| aaacaaatac gattagctac gaaattttat tgtagcaata aatttgtagc tatttgggta | 780 |
| atattgctac gacagttagc aattatagca aaaatgctaa attagctttg tcaatttaat | 840 |
| ttttagcta aattttttta taaaattgta aatagccatg aaattttaat ttttgtggct | 900 |
| attgttaggt attagccaca attttcatat atgtatctaa gaattttgtag ctatatatac | 960 |
| ataatgttgt agtggcaaat tctaacattg taagcttagc tgcccttttt tttttttttt | 1020 |
| tttggctaca aaactctaaa gtaaaggaac tagaaaactc gtttggcgag agaaagaggg | 1080 |
| atccatg | 1087 |

<210> SEQ ID NO 5
<211> LENGTH: 2896
<212> TYPE: DNA
<213> ORGANISM: Artificial sequence
<220> FEATURE:
<223> OTHER INFORMATION: TPS02b promoter/uidA gene fusion

<400> SEQUENCE: 5

| | |
|---|---|
| aagcttaatt tattttttgta aaacttctct aattttttgga caaactctta tattgatttt | 60 |
| ttaatcaaag ccaaaatatt tatttaacta tgaaaaaatt ttaacaacta atttattatg | 120 |
| gtaaataata ttgatatggt aacttcaagc acatgacaaa aattataact aactgcagaa | 180 |
| gtttattgtc tctctgaatc ttgtggctat atcataacaa atacttgtag ctaataagcc | 240 |
| aacgatgttc tcggtttcat ataatttgag ttttaaaata gttttaaat ttaatattta | 300 |
| tttcaaatca ttattgtggc taacatgtta taatcgcagt aatatttgga ggtgcaatac | 360 |
| ttatatttag ctacaaaatt ttattgtatc agaataagtt tgtagccatt aagttagttt | 420 |
| tcgccacaaa ttttataat tgaagcaaaa atacttattc agctacagca ttttgtatcg | 480 |

| | |
|---|---|
| agtaatatttt cgtgactaga agattaatat tgctacagta atttcagacg tgtggcaaaa | 540 |
| actcataatt agctacaaaa tattgtcgta gcaataattt tttatatcta ttaatgcaat | 600 |
| tattactaca tgcttttata acttgaggca aaaatatcta atagctataa cattttgtta | 660 |
| gaagtaattt ttgtggctat aaaattggta ttgctacagt aatttcaaat gcgtggcaaa | 720 |
| aaaatacgat taactacgaa atttttattgt agcaataact tgtagctat ttgggtaata | 780 |
| ttgctacgac agttagcaat tatagcaaaa atgctaaatc agctttgtca atctaatttt | 840 |
| gtagctaatt ttttatgaa attgtaaata gctatgaaat tttaattttt gtggctattg | 900 |
| ttaggtatta gccacatata gctaagaatt tgtagctata tatacataat gttgtagtgg | 960 |
| caaattctaa cattgtacgc ttggctgccc tttttttttt ttttggctac aaaactctaa | 1020 |
| agtaaaggaa ctagaaaact cgtttggcga gagaagagg gatcccccgg tggtcagtc | 1080 |
| ccttatgtta cgtcctgtag aaaccccaac ccgtgaaatc aaaaaactcg acggcctgtg | 1140 |
| ggcattcagt ctggatcgcg aaaactgtgg aattgatcag cgttggtggg aaagcgcgtt | 1200 |
| acaagaaagc cgggcaattg ctgtgccagg cagttttaac gatcagttcg ccgatgcaga | 1260 |
| tattcgtaat tatgcgggca acgtctgta tcagcgcgaa gtctttatac cgaaaggttg | 1320 |
| ggcaggccag cgtatcgtgc tgcgtttcga tgcggtcact cattacggca aagtgtgggt | 1380 |
| caataatcag gaagtgatgg agcatcaggg cggctatacg ccatttgaag ccgatgtcac | 1440 |
| gccgtatgtt attgccggga aaagtgtacg tatcaccgtt tgtgtgaaca cgaactgaa | 1500 |
| ctggcagact atcccgccgg gaatggtgat taccgacgaa aacggcaaga aaaagcagtc | 1560 |
| ttacttccat gatttcttta actatgccgg aatccatcgc agcgtaatgc tctacaccac | 1620 |
| gccgaacacc tgggtggacg atatcaccgt ggtgacgcat gtcgcgcaag actgtaacca | 1680 |
| cgcgtctgtt gactggcagg tggtggccaa tggtgatgtc agcgttgaac tgcgtgatgc | 1740 |
| ggatcaacag gtggttgcaa ctggacaagg cactagcggg actttgcaag tggtgaatcc | 1800 |
| gcacctctgg caaccgggtg aaggttatct ctatgaactg tgcgtcacag ccaaaagcca | 1860 |
| gacagagtgt gatatctacc cgcttcgcgt cggcatccgg tcagtggcag tgaagggcga | 1920 |
| acagttcctg attaaccaca aaccgttcta ctttactggc tttggtcgtc atgaagatgc | 1980 |
| ggacttgcgt ggcaaaggat tcgataacgt gctgatggtg cacgaccacg cattaatgga | 2040 |
| ctggattggg gccaactcct accgtacctc gcattaccct tacgctgaag agatgctcga | 2100 |
| ctgggcagat gaacatggca tcgtggtgat tgatgaaact gctgctgtcg gctttaacct | 2160 |
| ctctttaggc attggtttcg aagcgggcaa caagccgaaa gaactgtaca gcgaagaggc | 2220 |
| agtcaacggg gaaactcagc aagcgcactt acaggcgatt aaagagctga tagcgcgtga | 2280 |
| caaaaaccac ccaagcgtgg tgatgtgag tattgccaac gaaccggata ccgtccgca | 2340 |
| aggtgcacgg gaatatttcg cgccactggc ggaagcaacg cgtaaactcg acccgacgcg | 2400 |
| tccgatcacc tgcgtcaatg taatgttctg cgacgctcac accgatacca tcagcgatct | 2460 |
| ctttgatgtg ctgtgcctga accgttatta cggatggtat gtccaaagcg gcgatttgga | 2520 |
| aacggcagag aaggtactgg aaaaagaact tctggcctgg caggagaaac tgcatcagcc | 2580 |
| gattatcatc accgaatacg gcgtggatac gttagccggg ctgcactcaa tgtacaccga | 2640 |
| catgtggagt gaagagtatc agtgtgcatg gctggatatg tatcaccgcg tctttgatcg | 2700 |
| cgtcagcgcc gtcgtcggtg aacaggtatg gaatttcgcc gattttgcga cctcgcaagg | 2760 |
| catattgcgc gttggcggta acaagaaagg gatcttcact cgcgaccgca aaccgaagtc | 2820 |

```
ggcggctttt ctgctgcaaa aacgctggac tggcatgaac ttcggtgaaa aaccgcagca    2880
gggaggcaaa caatga                                                   2896
```

<210> SEQ ID NO 6
<211> LENGTH: 12
<212> TYPE: DNA
<213> ORGANISM: Artificial sequence
<220> FEATURE:
<223> OTHER INFORMATION: Motif 1

<400> SEQUENCE: 6

```
kktcgtwgca wt                                                         12
```

<210> SEQ ID NO 7
<211> LENGTH: 10
<212> TYPE: DNA
<213> ORGANISM: Artificial sequence
<220> FEATURE:
<223> OTHER INFORMATION: Motif 2

<400> SEQUENCE: 7

```
agtaatwtyw                                                            10
```

<210> SEQ ID NO 8
<211> LENGTH: 10
<212> TYPE: DNA
<213> ORGANISM: Artificial sequence
<220> FEATURE:
<223> OTHER INFORMATION: Motif 3

<400> SEQUENCE: 8

```
ttgtagcwaw                                                            10
```

<210> SEQ ID NO 9
<211> LENGTH: 171
<212> TYPE: DNA
<213> ORGANISM: Nicotiana sylvestris
<220> FEATURE:
<221> NAME/KEY: CDS
<222> LOCATION: (1)..(171)

<400> SEQUENCE: 9

```
atg agt caa tca att tct cca tta atg ttt tct cac ttt gca aaa ttt     48
Met Ser Gln Ser Ile Ser Pro Leu Met Phe Ser His Phe Ala Lys Phe
1               5                   10                  15 cag tcg aat att tgg aga tgc aat act tct caa ctc aga gtt ata cac    96
Gln Ser Asn Ile Trp Arg Cys Asn Thr Ser Gln Leu Arg Val Ile His
            20                  25                  30 tca tca tat gcc tct ttt gga ggg aga aga aaa gag aga gta aga aga   144
Ser Ser Tyr Ala Ser Phe Gly Gly Arg Arg Lys Glu Arg Val Arg Arg
        35                  40                  45 atg aat cga gca atg gat ctt tct tca                                171
Met Asn Arg Ala Met Asp Leu Ser Ser
    50                  55
```

<210> SEQ ID NO 10
<211> LENGTH: 57
<212> TYPE: PRT
<213> ORGANISM: Nicotiana sylvestris

<400> SEQUENCE: 10

```
Met Ser Gln Ser Ile Ser Pro Leu Met Phe Ser His Phe Ala Lys Phe
1               5                   10                  15

Gln Ser Asn Ile Trp Arg Cys Asn Thr Ser Gln Leu Arg Val Ile His
```

```
              20                  25                  30
Ser Ser Tyr Ala Ser Phe Gly Gly Arg Arg Lys Glu Arg Val Arg Arg
        35                  40                  45

Met Asn Arg Ala Met Asp Leu Ser Ser
    50                  55

<210> SEQ ID NO 11
<211> LENGTH: 29
<212> TYPE: DNA
<213> ORGANISM: Artificial sequence
<220> FEATURE:
<223> OTHER INFORMATION: primer

<400> SEQUENCE: 11
ctaagcttaa tttatttttg taaaacttc                                    29

<210> SEQ ID NO 12
<211> LENGTH: 30
<212> TYPE: DNA
<213> ORGANISM: artificial sequence
<220> FEATURE:
<223> OTHER INFORMATION: primer

<400> SEQUENCE: 12
atggatccct ctttctctcg ccaaacgagt                                   30

<210> SEQ ID NO 13
<211> LENGTH: 29
<212> TYPE: DNA
<213> ORGANISM: Artificial sequence
<220> FEATURE:
<223> OTHER INFORMATION: primer

<400> SEQUENCE: 13
tggatcctga agaaagatcc attgctcga                                    29

<210> SEQ ID NO 14
<211> LENGTH: 44
<212> TYPE: DNA
<213> ORGANISM: artificial sequence
<220> FEATURE:
<223> OTHER INFORMATION: primer

<400> SEQUENCE: 14
ctaatacgac tcactatagg gctcgagcgg ccgcccgggg aggt                   44

<210> SEQ ID NO 15
<211> LENGTH: 8
<212> TYPE: DNA
<213> ORGANISM: artificial sequence
<220> FEATURE:
<223> OTHER INFORMATION: primer

<400> SEQUENCE: 15 acctcccc                                                            8

<210> SEQ ID NO 16
<211> LENGTH: 27
<212> TYPE: DNA
<213> ORGANISM: artificial sequence
<220> FEATURE:
<223> OTHER INFORMATION: primer

<400> SEQUENCE: 16
ggatcctaat acgactcact atagggc                                      27
```

```
<210> SEQ ID NO 17
<211> LENGTH: 26
<212> TYPE: DNA
<213> ORGANISM: artificial sequence
<220> FEATURE:
<223> OTHER INFORMATION: primer

<400> SEQUENCE: 17
agaggcatat gatgagtgta taactc                                          26

<210> SEQ ID NO 18
<211> LENGTH: 18
<212> TYPE: DNA
<213> ORGANISM: artificial sequence
<220> FEATURE:
<223> OTHER INFORMATION: primer

<400> SEQUENCE: 18
ctatagggct cgagcggc                                                   18

<210> SEQ ID NO 19
<211> LENGTH: 25
<212> TYPE: DNA
<213> ORGANISM: artificial sequence
<220> FEATURE:
<223> OTHER INFORMATION: primer

<400> SEQUENCE: 19
acctccaaat attcgactga aattt                                           25

<210> SEQ ID NO 20
<211> LENGTH: 25
<212> TYPE: DNA
<213> ORGANISM: artificial sequence
<220> FEATURE:
<223> OTHER INFORMATION: primer

<400> SEQUENCE: 20
gtcatgtgct tgaagttacc atatc                                           25

<210> SEQ ID NO 21
<211> LENGTH: 26
<212> TYPE: DNA
<213> ORGANISM: artificial sequence
<220> FEATURE:
<223> OTHER INFORMATION: primer

<400> SEQUENCE: 21
gttaccatat caatattatt taccat                                          26

<210> SEQ ID NO 22
<211> LENGTH: 1796
<212> TYPE: DNA
<213> ORGANISM: Nicotiana sylvestris

<400> SEQUENCE: 22
gaattcacta gtgatttgag ctcaaagagg tgaaacctaa tctagtatgc aaaccatgtt     60
aaattctcaa ttgttttgat agataatgag ttttctgata attaataaat tattagataa    120
ttaaaggacc aaatttatat gacttttgtt ttttatcatc ttgatcatat atacaatgta    180
atggatacaa gcttatagtt gtataaaattc tatataatta gttattcata cattaattag    240
atatattcaa ttgttcttta taaatataat tcaaacctga aagcaatact tattttgtaa    300
```

```
gaattgcaat attgttattt tgttatggac ttaaatatta accatgttat aatcttaagt      360
ttatattatt agaaaaactt agtttttgaa agactaatat gaacattagt acttatttca      420
aaaataagcg cttagatata tgaaattact ttaagtactt atttaaaata attaagtacc      480
acacatacat acatatctct acaaactgtt aaagttttct atatgagtac ttattttaaa      540
ataagagcat aaatataata aattatgtta aattcttatt taaaataata aaggaccaaa      600
catgcataaa ataagtatg agcttaataa gtcaagaagc taattgataa gcattgatgc      660
caaatgcact tactaactgt tctatattgt aggaaaaatc taacttttat attaaaaatt      720
tattttcata aaacttccct aatttttgaa caaaatctta tattgatttt ttaatcaaag      780
ccaaaatatt tatttaacta tgaaaatttt ttaacaacta atttattatg gtaaataata      840
ttgatatggt aactttcagc acatgacaaa aattataact aactgcagaa gtttactgtc      900
tctctgaatc ttgtggctat gtcattctat cataacaaat acttgtagct aatacgccaa      960
cgatgttctc gatttcatat aatttgaatt ttaaaatagc ttttaaattt aatatttatt     1020
tcaaatcatt attgtgacta acatgttata accgcagtaa tatttggaga tgcaatactt     1080
atatttagct acaaaatttt attgtatcat aataagtttg tagctattaa gttagttttt     1140
gccacaaatt tttataattg aagcaaaaat acctattcaa ctacaatatt ttgtatcgag     1200
taatattttg tgactagaag attaatatta ttacagtaat ttctgacgtg tggcaaaaac     1260
tcataattat ctcacaaaata ttgtcgtagc aataattttt tatatctatt aatccaatta    1320
ttgctacatg cttttataac ttgaggcaaa aatatctatt tagctataac attttgttag     1380
aagtaatttt tgtgactata aagttgttat tgctacagta atttcaaatg cgtggcaaaa     1440
aaaatacgat tagctacgaa atttttattgt agcaataaat ttgtagctat ttgggtaata    1500
ttgctacgac agttagcaat tatagcaaaa atgctaaatc agctttgtcg atttaatttt     1560
gtagctaatt tttttatgaa tttgtaaata gctatgaaat tttaattttt gtggctattg     1620
ttaggtatta gccacatata gctaagaatt tgtagctata tatacataat gttgtagtgg     1680
caaattctaa cattgtaagc ttggctgcct tttttttttt ttgggctaca aaactctaaa     1740
gtaaaggaac tagaaaactc gtttggcgag agaaagaggg atccataatc gaattc         1796

<210> SEQ ID NO 23
<211> LENGTH: 36
<212> TYPE: DNA
<213> ORGANISM: artificial sequence
<220> FEATURE:
<223> OTHER INFORMATION: primer

<400> SEQUENCE: 23
tgagctcaaa gaggtgaaac ctaatctagt atgcaa                                 36
```